United States Patent [19]

Bloch et al.

[11] 4,341,038
[45] Jul. 27, 1982

[54] OIL PRODUCTS FROM ALGAE

[76] Inventors: Moshe R. Bloch, 11 Assaf Simchoni, Beer Sheva; Joel Sasson, Hapalmach 30, Jerusalem; Margaret E. Ginzburg, 1 Dakar Alley, French Hill, Jerusalem, all of Israel; Zvi Goldman, 24 Diamond Ledge Rd., Stafford Springs, Conn. 06076; Ben Z. Ginzburg, 1 Dakar Alley, French Hill, Jerusalem, Israel; Nissim Garti, Alroi 5-B, Jerusalem, Israel; Asher Porath, Kubovi 12, Jerusalem, Israel

[21] Appl. No.: 165,251

[22] Filed: Jul. 2, 1980

[30] Foreign Application Priority Data

Jul. 3, 1979 [IL] Israel ............................... 57712

[51] Int. Cl.³ .......................................... A01G 7/00
[52] U.S. Cl. ................................................ 47/1.4
[58] Field of Search ..................................... 47/1.4

[56] References Cited

U.S. PATENT DOCUMENTS 4,115,949 9/1978 Avron et al. ........................ 47/1.4
4,199,895 4/1980 Avron et al. ........................ 47/1.4

OTHER PUBLICATIONS

High-Energy Chemicals Out of Thin Air, Science News, Weizmann Inst., Rehovot, Israel, Issue 12, Dec. 1975.
Conversion of Halophilic..., Goldman et al., Fuel, vol. 59, Mar. 1980, IPC Sci. & Tech. Press, pp. 181-184.

Primary Examiner—Robert E. Bagwill
Attorney, Agent, or Firm—Browdy and Neimark

[57] ABSTRACT

Oil products and a high nitrogen content residue are obtained by growing halophilic algae in saline solution, harvesting an algae-salt water slurry, solvent extracting said slurry, and recovering the product and residue. Use of a growth promoting enzyme, salt concentration gradients for harvesting, and water insoluble solvents at elevated temperatures are preferred.

23 Claims, 1 Drawing Figure

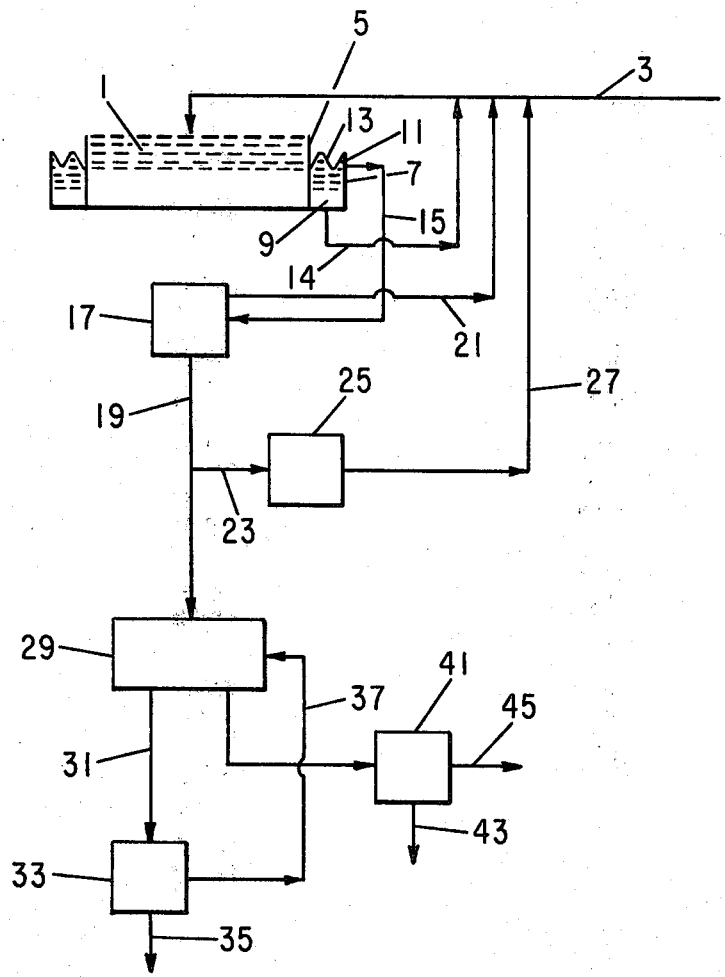

OIL PRODUCTS FROM ALGAE

TECHNICAL FIELD

The present invention relates to the cultivation of certain types of halophilic algae and to the production of fuel-like products from such algae. The invention furthermore relates to the production of various other valuable byproducts. The invention also relates to the process of cultivation and harvesting of algae. Other and further features of the invention will become apparent hereinafter.

BACKGROUND OF THE ART

Halophile algae, especially of the Dunaliella type, grow in nature in aqueous media having a high salt content, such as salterns. Such algae can be cultivated in order to obtain a convenient source of lipids, carotenes, proteins, glycerol and of hydrocarbon mixtures essentially similar to fossil oil. See, for example, U.S. Pat. No. 4,115,949. For such cultivations, the conditions must be suitably adapted.

One of the main limitations in the cultivation of halophilic algae in salty solutions is the velocity of transfer of carbon dioxide from air into the solution. Exchange with the atmosphere results in a surface layer, which serves as source of carbon dioxide for lower layers of higher alkalinity, which have become depleted of carbon dioxide due to the metabolism of the algae. A further limiting factor is the low velocity of conversion of carbon dioxide to $H_2CO_3$ when dissolved in brine. Satisfactory conditions of cultivation can be provided by replenishing evaporated water in a suitable manner and by adding certain additives adapted to further the rate of growth of said algae and, if required, by adding fertilizers.

BRIEF SUMMARY OF THE INVENTION

The present invention relates to the cultivation and harvesting of halophile algae, especially of the Dunaliella type, and to a proess for the recovery from such algae of oil products useful as a source of energy, specifically as fuel or as a chemical feedstock.

More particularly, there has now been found a process for obtaining oil products from algae which comprises (a) growing halophilic, unicellular, swimming algae, having no cell walls, in a saline solution; (b) harvesting said algae to obtain an algae-salt water slurry; (c) extracting oil products from said slurry employing a solvent for said products; and (d) recovering said oil products and an algae residue.

BRIEF DESCRIPTION OF THE DRAWING

The drawing is a schematic representation of the process according to a preferred embodiment including growth, concentration, extraction, and recycle/replenishment.

DETAILED DESCRIPTION OF THE INVENTION

According to one feature of the present invention, the rate of hydration of carbon dioxide in salt solutions is substantially increased by adding to said salt solutions a suitable quantity of an enzyme contained in such halophile algae. Said enzyme, carbonic anhydrase, speeds up the absorption of carbon dioxide and enhances its availability to the growing algae. The enzyme is contained in the algae, and it is obtained in a form suited for the intended purpose by opening up said algae mechanically or by osmotic action. The liberated enzyme is admixed to the growth medium, and such addition results in a substantially increased rate of cultivation of the algae and thus in improved yields per unit time. Part of the algae is advantageously ground, and the resulting material is recycled and added to the growth medium. This results in an enhanced rate of propagation of the algae culture. The algae may be ruptured mechanically as by passage through a centrifugal pump, or they may be ruptured by introduction into sweet water or dilute saline below seawater concentration, i.e., less than 0.2 M NaCl. Comparatively small quantities of ground or ruptured algae are required, and the required quantity is established periodically by conventional tests. The enzyme, carbonic anhydrase, enhances the growth rate of the algae.

According to a further aspect of the invention, the need for expensive and complicated agitation, aeration, or carbonation of the solution in the growth pond pan is eliminated. When the uppermost layer of the pond is subjected to evaporation, salt concentration of the surface layer increases and with it the density of this layer, thus causing it to sink to a lower layer pushing up solution from a lower layer to the uppermost part, where it is enriched in carbon dioxide and where part of its water content is evaporated. The lower layers are rendered more alkaline by the metabolism of the growing algae. The effect can be utilized in a convenient manner if the surface layer is of a concentration virtually that of the bulk. Water, or aqueous salt solution, must be added from time to time to replenish water lost by evaporation.

According to the present invention, the aqueous medium added to replenish water lost by evaporation is added to that portion of the growth solution which is recirculated after removal of algae for processing so that its salt concentration becomes lower than that of the bulk of the solution in the growth pond solution at the point of addition so that upon evaporation the upper layer will become heavier than the bulk of the solution and sink. The salt concentration of the added solution is smaller than that of the average of the bulk of the pond. The added solution may be made up from seawater or by starting with brackish water. From time to time, it may be necessary to purge a portion of the recirculating growth solution to prevent buildup of impurities. When this is done, "pure" salt is added to achieve the desired concentration. It is preferred that the addition is effected at nighttime. According to a preferred embodiment, algae ground up by a pump are added to the replenishment solution. The added solution may be preheated, and it is advantageously added during periods of extremes of the temperature cycle. Wind conditions are taken into consideration. The water can be heated in a "solar pond."

The cultivation of halophile algae proceeds at a higher rate when the enzymes defined above are admixed and when the surface layer is replenished so as to enrich the culture medium with an adequate quantity of carbon dioxide.

While floating suction dredgers and thickening drums or filters can be used, the separation of the algae from the growth medium is preferably based on the observation that when brine of lesser salt concentration than that of the bulk of the growth medium forms a layer above the growth medium, this surface layer forms a trap for the algae which do not burst but attain a concentration many times that in the bulk of the medium. This supernatant liquor, containing a large percentage of the intact algae is decanted or removed in any other convenient manner and further thickened, e.g., by centrifuging or filtering. It is convenient to have the supernatant liquor of lower salt concentration flow either countercurrent or concurrent with the growth liquor to the decantation point, the latter being preferred at this time.

According to a preferred embodiment, the area of collection, i.e., the area of the stream flowing in the top layer is constricted by mechanical means. This can be attained by providing channel-formed members which dip to a certain depth into the growth medium and in which said lighter upper layer flows to the point of collection. By thus restricting the area of contact between the collection (or concentrating) solution and the bulk of the growth solution, the concentrating effect is enhanced and less water is ultimately required to be removed.

By establishing a concentration gradient between the bulk of the medium in which the algae are cultivated and an upper layer, said upper layer being of a lower salt concentration than the lower one, the concentration of the algae is substantially enriched in the low-concentration layer. It seems that these are trapped in the layer of lower salt concentration and do not return to the layer of the higher salt concentration. Comparatively small concentration gradients are sufficient in order to bring about a substantial concentration. If, for example, the algae are grown in a medium containing about 11.7 percent sodium chloride, to a content of 0.025 percent wet weight, and if there is established over this a layer of about 10 percent sodium chloride, the area of the two layers being in a ratio of about 100:1 (by carrying out the experiment in a flask of 10 cm diameter with a neck of 1 cm diameter where the solution of lower concentration is provided), after about 100 minutes, there is obtained a concentration of algae in the upper layer of about 0.9 percent by weight, i.e., a concentration of about 36-fold. The suspension of higher concentration, i.e., of 0.9 percent algae content, may be used for a further concentration step, forming the lower layer, with an upper layer of 8.5 percent salt concentration. After a further 100 minutes, the concentration of algae in the upper layer was 3.8 percent, i.e., an overall increase of concentration of about 150-fold. This illustrates a concentration process under static conditions.

The concentration can also be effected under dynamic conditions. For example, a channel having inwardly tapered sidewalls was charged with algae culture having a content of 0.025 percent wet algae, and this was maintained at a flow rate of about 20 cm/min in the channel. On top of this layer, there was provided a layer of salt solution of 85 percent of the salt content of the lower layer (10 percent), and this flowed in the same direction. After 60 minutes' flow, there was attained a concentration of 0.25 percent (10-fold increase) in the upper layer. When this was used as the lower layer in a similar run, this time the concentration of the upper layer being 8.5 percent salt, a further concentration from 0.25 percent to 2 being algae was attained during a further 60 minutes. The upper layer is of considerably smaller thickness, and the area of interface between layers is restricted. Substantially no mixing takes place between the layers if these are introduced carefully into the channel-like structure.

Similar experiments were carried out with solution concentrations of 11.7 percent to 3.5 percent (30 percent), and the algae concentration factor was similar to that obtained in the above-described experiment.

After the algae have been harvested and, preferably, after further thickening or concentration of the algae content, for example, by mechanical means such as centrifuging or filtration, or chemically by raising the pH, for example, using an alkali metal, alkaline earth metal, or ammonium hydroxide (especially sodium, calcium, or ammonium hydroxide), the concentrated sludge of algae-salt water is treated to extract the oil products. It has been found that this can be accomplished without removal of the water and/or salt by treatment with a suitable solvent, such as hydrocarbons (e.g., toluene, xylene, and especially benzene), water immiscible alcohols (e.g., butanol, amyl), chlorinated hydrocarbons (e.g., methylene chloride, chloroform), or by using the oil products obtained from an earlier extraction. Preferred solvents are water insoluble. While the term "extraction" is employed, it is thought that a good portion of the oil products results from conversion of various materials in the algae, e.g., proteins and lipids, under the conditions of treatment described below. It is surprising and extremely advantageous that the extraction can occur in the presence of both salt and water since earlier methods for extracting fuels from such materials depended, for example, upon reductive hydrogenation of a dried material, this obviously requiring catalysts and the expenditure of energy to remove water. The oil products obtained, particularly from the relatively low temperature extraction steps, are characterized by having a carbon and hydrogen content and calorie value similar to that of crude oil. Also characteristic of the low temperature oil products are extremely low (less than 1 percent) nitrogen contents. While the higher temperature extraction increases the degree of conversion and hence total yield of fuel-like materials, an increase in nitrogen and oxygen is noted.

The first extraction step may be carried out at ambient temperature but preferably at temperatures in the range of 60° C. to 120° C. by means of benzene or other suitable solvent. This results in the extraction of about 16.5 percent by weight of the dry weight of the algae, which extract is in the form of hydrocarbon chains, fats, waxes and the like. This fraction has no appreciable content of nitrogen (less than 1.0 and often less than 0.5 percent). As temperatures increase above 120° C., the nitrogen content of the product increases, lessening its value. The solvent used can be recovered substantially in a quantitative manner and recycled.

The final extraction step is effected with the same solvents, but at elevated temperatures and corresponding pressure, of above 200° C., especially up to 350° C., and preferably 280° C. to 350° C. This results in the further extraction of about 30 percent by weight of the initial weight of the dry algae, and this gives a fraction having a certain nitrogen content, and containing compounds of C-20 to C-30. Both fractions do not contain appreciable quantities of sulfur. Preferably, prior to the final extraction, the residue from the earlier extraction is thickened to further reduce water content. This can be accomplished by filtration after separation of the solvent-oil product layer.

Depending upon the intended use for the final oil product (products), it may be desirable to effect extraction in more than two stages. For example, an intermediate extraction at about 150° C., easily obtainable with steam, yields a product different in composition from either the higher or lower temperature extraction.

The extraction can also be effected in a one-step extraction process. If this is effected with benzene at about 300° C. during 1 hour, about 65 percent of the initial carbon content is extracted in the form of a fuel-like substance, which is recovered from the benzene, which is used for further extraction steps. It is thought that the increased overall yield of oil products may be attributed in part to the presence of glycerol which is converted to oil products at elevated temperatures. Since glycerol is water soluble, portions at least may have been lost with the filtrate in a multi-stage process.

When batches of Dunaliella sludge were extracted, there was obtained by the first extraction a water-insoluble extract which contained about 25 to 35 percent of the carbon content of the original algae. This extract contained about 85 to 89 percent carbon, about 9 to 10 percent hydrogen and less than 1 percent nitrogen. It is obtained as viscous oil and has a very low sulfur content. When the residue is extracted with benzene at 250° C. and at about 150 atmospheres, the extract obtained has a slightly lower carbon content (about 72 to 76 percent), a nitrogen content of about 6 to 7 percent and contains about 25 to 35 percent of the initial carbon content of the algae. The product is a brown viscous oil containing less than 0.1 percent sulfur. The organic residue can be worked up and, due to its high nitrogen content, valuable foodstuffs and fertilizer can be obtained besides the oil-like products of pyrolysis if the heating is taken to above 300° C.

The process of the present invention can be carried out with a variety of halophilic algae. The primary criteria, in addition to their oil-producing ability, are mobility and a lack of cell walls. Mobility is important to the concentrating technique since the ability to swim to a salt solution having a lower concentration constitutes an important separation technique. The lack of cell walls, in addition to being a condition which apparently triggers the oil-forming properties, also makes it possible to extract the products with ease and to obtain a dry residue having a high nitrogen content and hence value as animal feed or fertilizer. While multi-celled algae would be attractive in theory, no varieties having the foregoing criteria are known at present. The preferred genus at this time is Dunaliella and especially Dunaliella parva. Particularly, Dunaliella Parva Dead Sea Ginzburg, D. parva Lerche 19/9, and A8 Red, have been successfully employed. All three are publicly available at the Cambridge Algal Collection, Torey Way, Cambridge, United Kingdom.

Cultivation is best effected in ponds in an aqueous medium containing about 6 to 25 percent by weight of sodium chloride and other required nutrients (e.g., N, P, Fe, Trace elements). The aqueous salt solution added contains more salt than the lowest concentration and less than the highest concentration in the pond. The replenishing solution is advantageously enriched by finely-ground algae or by enzyme extracted from such algae. Growth of algae is intended to refer both to number of algae per volume and concentration of oil product and precursors in the algae. Some parameters influencing these factors are known to the art (see U.S. Pat. No. 4,115,949, for example).

The invention is illustrated with reference to the enclosed schematical drawing, now according to scale, which is a top view schematical flow scheme of a growth, collection, and extraction arrangement of the invention.

The algae are grown in pond 1 which is replenished via pipe 3, emptying into the center of pond 1, with the required mix of salt, nutrients, etc. The algae-containing growth solution overflows weir 5 into channel 7 to form a bottom layer 9 of a relatively highly-concentrated salt solution over the top of which flows a layer 11 of more dilute salt solution which serves to concentrate the algae therein. The area of interlayer contact is restricted, for example, by a corrugated member 13. The concentrated salt solution is recycled to the pond via line 14 while the solution into which the algae have concentrated is removed via line 15 to a mechanical concentrating device 17 such as a centrifuge. From device 17, the supernatant liquid is generally returned to the pond via line 21 while the now further-enriched algae-salt water solution exits via line 19. A portion of this product stream is removed as required via line 23 to a device 25, such as a grinder, which ruptures the algae, releasing the enzyme for recycle to the growth pond via line 27. The majority of the concentrated algae solution passes to the extraction-separation device 29 wherein it is contacted with, for example, benzene, at elevated temperature and pressure. The oil products then leave device 29 via line 31 together with the benzene for a separation device 33 from which exits the oil products via line 35 and benzene via line 37 for recycle to the extractor/separator 29. The other stream exiting device 29 via line 39 is the remaining algae-salt water residue which may be washed and filtered in device 41, resulting in a waste material exiting via line 45 and a high nitrogen residue in line 43.

The added growth medium advantageously comprises about 3 parts by volume ocean water and salt to establish a concentration of at least 5 to 6 percent sodium chloride by weight. Advantageously about 1 percent by weight of ground up algae are added. The rate of replenishment depends on the rate of evaporation and withdrawal of algae, and it is in the order of about 1 cm depth, i.e., about 10 liter per square meter per day. In the pond, the concentration of salt is advantageously maintained at about 10 to 15 percent salt, with the maximum quantity of carbon dioxide possible.

EXAMPLE 1

A pond, about 10 cm deep, was filled with a 10 percent by weight solution of sodium chloride and nutrients, made up from ocean water. The pond was exposed to sunlight at ambient temperature and seeded with Dunaliella parva Lerche 19/9 0.5 g/liter, i.e., 0.05 percent, which was cultivated in the pond without any artificial agitation. The growth rate of the algae was such that their concentration increased nearly two-fold per day. When a concentration of 0.75 percent was reached, algae were harvested: 0.25 percent were removed by harvesting and 0.5 percent remained, which were again cultivated to 0.75 percent.

The cultivation was repeated but with bubbling through of carbon dioxide in fine bubbles and with mechanical agitation. The rate of growth was the same as before.

The evaporated water was replaced by a solution as used at the start of the experiment, at a ratio of 7 mm added per day. A corresponding quantity of the algae suspension was removed for further treatment and for thickening. About 0.25 percent g/liter/day wet weight (0.1125 g dry weight) algae were harvested.

EXAMPLE 2

An enzymatically-active additive was prepared as follows. A suspension containing 100 grams algae (Dunaliella parva Lerche 19/9) per liter of water was centrifuged at about 1,000 gravities for 10 minutes to obtain a paste of about 70 percent algae by wet weight (31.5 percent dry weight). Distilled water was added to the paste, 50 parts by weight per 1 part algae concentrate. After standing for 15 minutes, the algae had ruptured into a form useful as an additive to the growth solution. (Such an additive can also be prepared by comminuting the algae by passage of the concentrated paste through a centrifugal pump.)

Dunaliella parva Lerche 19/9 was cultivated in a pond as in Example 1. To this growth solution was added a quantity of algae equivalent to 0.25 mg purified enzyme (carbonic anhydrase) per liter of water, that is, about 0.015 gram of dry weight algae per liter of water. Cultivation was carried out at 25° C. under sunlight, and the growth rate of the algae was 22.5 grams (dry weight) of algae per square meter per day or 0.375 gram per liter per day.

By comparison, without the use of the additive enzyme under the same conditions, the growth rate was only 0.25 gram per liter per day.

EXAMPLE 3

The harvested algae were thickened by conventional means, like low speed centrifugation, and the thus obtained sludge containing 60 percent wet weight algae was extracted with about 1 volume of light benzene or benzene per volume of sludge, having a content of about 350 g algae (dry weight) per liter sludge. This extraction was carried out below 40° C. and about 25 percent of the carbon content of the algae was thus extracted. The extract was mainly a hydrocarbon mixture, nearly no nitrogen content and less than 0.1 percent sulfur content. The organic liquid—35 g extract of about a further 40 percent of the C-content of the algae. This fraction has a content of about 7 percent of nitrogen, less 0.1 percent sulfur. The second fraction seems to have as main constituents hydrocarbons of about 20 to 30 carbon chains.

The residue has a high nitrogen content (about 12 to 14 percent nitrogen) and can be worked up and used as an animal foodstuff or feedstuff additive or it can be used as fertilizer.

The first extracted fraction was analyzed and found to contain 88 percent C, 9.5 percent H, 2 percent O and about 0.5 percent N.

The second fraction contains about 76 percent C, 10 percent H, 7 percent N, and 7 percent O.

EXAMPLE 4

Following cultivating, harvesting, and concentration to an algae-salt water slurry containing 300 g/l dry weight algae (Dunaliella parva Dead Sea Ginzburg), to 0.2 liter of slurry is added 0.2 liter of benzene. The mixture is then heated at 40° C. for 360 minutes, and the resulting benzene fraction is separated by decantation. After removing the benzene by evaporation, there remains 7.2 grams of an oil product containing 88.4 percent C, 8.4 percent H, 2.8 percent O, and 0.3 percent N and having a calorie value of 10 kilocalories per gram.

The aqueous residue from the first extraction is then filtered and water washed. The remaining 43.8 grams of damp residue are then contacted with 0.2 liter of benzene in an autoclave and heated to 300° C. under a pressure of 200 atmospheres for 120 minutes. After separation from the residue and removal of the benzene, there remains 15.1 grams of an oil product containing 75.4 percent C, 9.2 percent H, 9.6 percent O, and 5.8 percent N and having a caloric value of 8.5 kilocalories per gram.

The foregoing procedure was repeated with the indicated species of algae, yielding the following results:

| Species | Extract | Yield (%) | % C | % H | % O | % N | Kilocalories per gram |
|---|---|---|---|---|---|---|---|
| D. parva Lerche 19/9 | 1 | 15.7 | 85.2 | 8.3 | 6.2 | 0.2 | 9.5 |
|  | 2 | 25.8 | 78.0 | 9.3 | 6.8 | 5.7 | 8.7 |
| A8 Red | 1 | 18.4 | 89.3 | 8.5 | 1.7 | 0.4 | 9.7 |
|  | 2 | 22.1 | 73.8 | 10.4 | 8.8 | 6.9 | 8.4 |

EXAMPLE 5

To illustrate a single step extraction process, a slurry identical to that first described in Example 4 is employed. To 0.2 liter of slurry is added 0.2 liter of benzene. The mix is heated to 300° C. in an autoclave at 200 atmospheres for 120 minutes. After separation from the residue and removal of the benzene, there remains 24 grams of an oil product analyzing 80.2 percent C, 8.3 percent H, 6.2 percent O, and 5.3 percent N and having a caloric value of 8.4 kilocalories per gram.

EXAMPLE 6

The first stage extraction of Example 4 is repeated using 0.02 liter of slurry and 20 grams of a previous first stage extraction oil product. After a temperature of 80° C. for 600 minutes, a total of 20.72 grams of oil product is recovered analyzing 84.1 percent C, 8.0 percent H, 7.5 percent O, and 0.4 percent N and having a caloric value of 8.9 kilocalories per gram.

What is claimed is:

1. A process for obtaining oil products from algae, which process comprises:
   (a) growing halophilic, unicellular, swimming algae, having no cell walls, in a saline solution and in the presence of carbonic anhydrase enzyme derived from such algae;
   (b) harvesting said algae to obtain an algae-salt water slurry;
   (c) extracting oil products from said slurry employing a solvent for said products; and
   (d) recovering said oil products and an algae residue.

2. A process for obtaining oil products from algae, which process comprises:
   (a) growing halophilic, unicellular, swimming algae, having no cell walls, in a saline solution and in the presence of carbonic anhydrase enzyme derived from such algae;
   (b) concentrating and harvesting said algae by contacting the algae-containing growth solution with a second saline solution having a salt content of from 30 to 90 percent of that of the growth solution, thereby obtaining an algae-salt water slurry;
   (c) extracting oil products from said slurry employing a solvent for said products; and
   (d) recovering said oil products and an algae residue.

3. A process for obtaining oil products from algae, which process comprises:

(a) growing halophilic, unicellular, swimming algae, having no cell walls, in a saline solution and in the presence of carbonic anhydrase enzyme derived from such algae;
(b) harvesting and concentrating said algae to obtain an algae-salt water slurry;
(c) extracting oil products from said slurry by contacting same with a water insoluble solvent for the oil products at a temperature between ambient and about 350° C.; and
(d) recovering said oil products and an algae residue.

4. A process as in claim 1, 2, or 3 wherein said carbonic anhydrase is added to the saline solution of step (a).

5. A process as in claim 4 wherein the source of carbonic anhydrase is at least in part ruptured algae.

6. A process as in claim 5 wherein the algae is mechanically ruptured.

7. A process as in claim 5 wherein the algae is ruptured by contact with water having a salt content of less than 0.2 molar NaCl.

8. A process as in claim 5 wherein between 1 and 10 percent by weight of the harvested algae are ruptured and returned to the saline solution of step (a).

9. A process as in claim 1, 2, or 3 wherein the algae is from the genus Dunaliella.

10. A process as in claim 1, 2, or 3 wherein the concentration of the saline solution of step (a) is from 6 to 25 percent NaCl.

11. A process as in claim 1, 2, or 3 wherein the harvested algae is concentrated by separating the majority of water from the algae-salt water slurry.

12. A process as in claim 11 wherein the method of separation is by centrifuge.

13. A process as in claim 11 wherein the method of separation is by filtration.

14. A process as in claim 11 wherein the method of separation is by flocculation, effected by increasing the pH of the algae-salt water slurry.

15. A process as in claim 14 wherein the pH is increased by the addition to the slurry of an alkali metal, alkaline earth metal, or ammonium hydroxide.

16. A process as in claim 1, 2, or 3 wherein the solvent is selected from the group consisting of benzene and previously-extracted oil products.

17. A process as in claim 1, 2, or 3 wherein oil product is recovered from the slurry by distillation and a nitrogen rich material is recovered from the final organic residue.

18. A process as in claim 2 wherein the area of contact between the growth solution and the harvesting solution is less than the area of the growth solution prior to harvesting.

19. A process as in claim 3 wherein the extraction of step (c) is conducted in a single step at a temperature between 280° and 350° C.

20. A process as in claim 3 wherein the extraction of step (c) occurs in two stages, the first extraction being conducted at a relatively low temperature such that less than 1 percent nitrogen is found in the oil product and a second stage wherein the residue from the first step is contacted with the solvent at a higher temperature but less than 350° C.

21. A process as in claim 20 wherein the first step is conducted at a temperature within the range of 60° to 120° C. and the second step within a range of 280° to 350° C.

22. A process as in claim 20 wherein a portion of the water is removed from the residue from the first step prior to the second step extraction.

23. A process as in claim 20 wherein an intermediate extraction occurs at a temperature of about 150° C.

* * * * *